United States Patent
Hamadeh et al.

(10) Patent No.: US 10,952,735 B1
(45) Date of Patent: Mar. 23, 2021

(54) ADJUSTABLE UTERINE COMPRESSION APPARATUS FOR POSTPARTUM HEMORRHAGE

(71) Applicants: Sameer Ghazi Kasim Hamadeh, Alkhobar (SA); Nasreen Ghazi Kasim Hamadeh, Alkhobar (SA)

(72) Inventors: Sameer Ghazi Kasim Hamadeh, Alkhobar (SA); Nasreen Ghazi Kasim Hamadeh, Alkhobar (SA)

( * ) Notice: Subject to any disclaimer, the term of this patent is extended or adjusted under 35 U.S.C. 154(b) by 0 days.

(21) Appl. No.: 17/016,948

(22) Filed: Sep. 10, 2020

(51) Int. Cl.
*A61B 17/12* (2006.01)
*A61B 17/42* (2006.01)

(52) U.S. Cl.
CPC .............. *A61B 17/12* (2013.01); *A61B 17/42* (2013.01); *A61B 2017/12004* (2013.01); *A61B 2017/4216* (2013.01); *A61B 2560/04* (2013.01)

(58) Field of Classification Search
CPC ........ A61B 17/12004; A61B 17/12009; A61B 17/12013; A61B 17/42; A61B 17/4216; A61B 2017/12004; A61B 2017/12018; A61B 2017/4216; A61B 17/12; A61B 2017/00805; A61F 2/0031; A61F 2/0036; A61F 2/2481; A61F 2/0045; A61F 2/0063
See application file for complete search history.

(56) References Cited

U.S. PATENT DOCUMENTS

| | | |
|---|---|---|
| 8,795,292 B1 | 8/2014 | El-Dabh |
| 8,845,664 B2 | 9/2014 | Pedrick et al. |
| 9,271,738 B2 | 3/2016 | Ward et al. |
| 2003/0199888 A1* | 10/2003 | Lutze ................. A61B 17/1227 606/157 |
| 2005/0250977 A1* | 11/2005 | Montpetit ............. A61F 2/0045 600/29 |

(Continued)

FOREIGN PATENT DOCUMENTS

| | | |
|---|---|---|
| AU | 2017101567 A4 | 12/2017 |
| CN | 203988281 U | 12/2014 |

OTHER PUBLICATIONS

Belfort, "Postpartum hemorrhage: Management approaches requiring laparotomy", www.uptodate.com/contents/postpartum-hemorrhage-management-approaches-requi . . . (2019), 28 pages.

*Primary Examiner* — Katherine M Shi
*Assistant Examiner* — Lindsey Bachman
(74) *Attorney, Agent, or Firm* — Nath, Goldberg & Meyer; Richard C. Litman (57) ABSTRACT

The adjustable uterine compression apparatus for postpartum hemorrhage includes at least one belt adapted for encircling the uterus transversely, the belt having keeper loops so that the belt can be cinched to continuously adjust the degree of compression applied to the uterine arteries. The belt may also be shortened and used to apply compression to the ovarian arteries. Preferably, a plurality of belts are applied spaced apart axially along the body and cervix of the uterus. The belts may be applied separately and independently, or may be embedded or incorporated into a sheet or vest that may be applied posteriorly behind the uterus and further secured by straps extending over the fundus that are cinched to at least one of the transverse belts to apply axial compression, in addition to transverse compression of the uterus. The belt(s) and vest may be made of polyglactin mesh, so that they are bioabsorbable.

4 Claims, 5 Drawing Sheets

(56) References Cited

U.S. PATENT DOCUMENTS

| | | | |
|---|---|---|---|
| 2010/0234862 A1* | 9/2010 | Patel | A61B 17/12009 606/151 |
| 2012/0123450 A1* | 5/2012 | Forsell | A61F 5/0066 606/151 |
| 2017/0071630 A1* | 3/2017 | Weeks | A61B 17/12 |
| 2019/0069899 A1* | 3/2019 | Isch | A61B 17/12 |

* cited by examiner

ADJUSTABLE UTERINE COMPRESSION APPARATUS FOR POSTPARTUM HEMORRHAGE

BACKGROUND

1. Field

The disclosure of the present patent application relates to medical devices, and particularly to an adjustable uterine compression apparatus for postpartum hemorrhage.

2. Description of the Related Art

The uterus is a major component of the female reproductive system. During pregnancy, the uterus expands greatly in size to provide a safe, warm, and nourishing environment for growth of the fetus. The uterus has a convex upper portion called the fundus, to which the fallopian or uterine tubes are attached; a corpus or body extending below the fundus; a narrower cervix extending below the body; and a cervical canal defined within the cervix, which opens into the vagina. The uterus is attached to the pelvic wall and other internal pelvic organs by several ligaments, including the round ligaments, the cardinal ligaments, the uterosacral ligaments, and fibrous sheets covering a portion of the uterus referred to as the broad ligaments. The uterus receives its blood supply primarily from the ovarian artery and from the uterine artery, which has branches extending longitudinally down each side of the uterus.

During natural or vaginal childbirth, it is normal for the mother to lose some blood, perhaps up to one-half of a quart. When a Caesarian or C-section is needed, the mother will lose more blood, perhaps up to one quart. In natural childbirth, the birth of the baby is followed by expulsion of the placenta (which is connected to the infant by the umbilical cord until the cord is severed during delivery), usually about 30 minutes to one hour after birth. Normally, contractions will continue after expulsion of the placenta, and provide a natural mechanism for stopping bleeding, e.g., from where the placenta is detached from the uterine wall, and from other tissues of the uterus.

Some women, however, experience a complication of childbirth known a postpartum hemorrhage (PPH) in which excessive bleeding occurs and will not stop. It has been estimated that PPH affects between 1% and 5% of women during childbirth, and of those women afflicted with PPH, about 3% die, making PPH the largest cause of fatality in women undergoing childbirth. Left unchecked or untreated, PPH progressively leads to dizziness, nausea, and a severe drop in blood pressure, which may result in shock, and eventually to death.

PPH is often manifested by atony, a condition in which the muscles of the uterus are unable to continue contractions after birth or expulsion of the afterbirth. Atony is believed to be the leading cause of PPH. Other causes may include abnormal conditions affecting the placenta, including placental abruption (separation of the placenta from the uterus before birth); placenta accreta, placenta increta, or placenta percreta (conditions where the placenta grows into the uterine wall too deeply); placenta previa (the placenta lies low in the uterus and covers the cervix); side effects of anesthesia or medications; and tearing or lacerations, which may be incident to instruments or measures taken to assist in delivery of the baby. This list is not exhaustive, and other conditions have been implicated in causing PPH.

If the clinical presentation permits, the health care practitioner confronted by PPH will often try a conservative approach first, such as uterine massage or administering medications to try to reduce or stop the bleeding, particularly if there is a chance to avoid hysterectomy without too great a risk to the life of the mother. However, when the several uterine-saving approaches designed to manage postpartum hemorrhage due to uterine atony or abnormal placentation are attempted and the patient does not respond to conservative medical treatment, different invasive surgical approaches are possible prior to hysterectomy. They consist of uterine compression sutures, arterial ligations, and intrauterine tamponade combined with or without uterine compression sutures. The choice from these techniques depends mostly on the cause of bleeding and the skills of the surgeon. Controlling bleeding may require a combination of more than one approach.

Because of its variation in complexity, success rate, and hoping to improve its efficacy, these techniques have been studied and updated by many centers around the world. Uterine compression and arterial ligation procedures require case selection to ensure its success and effectiveness. Uterine artery ligations require skillful surgeons, and in addition, there is considerable risk of injuring adjacent organs, which makes the surgeons reluctant to perform some of these procedures. It will not wholly control bleeding from uterine atony or placenta accreta, but may decrease blood loss while other interventions are being attempted. On occasion, if the procedure only achieves limited success or the patient has a recurrence of severe bleeding, it may be necessary to remove the ligation sutures and replace them with ligation sutures that are better positioned or more effective in stopping or reducing the bleeding, which is another difficult, time-consuming, and traumatic surgical procedure for the patient.

Applying uterine compression sutures is traumatic, and necessitates a special widespread curved needle with long suture, opening the uterine cavity or penetrating the uterus. It's time-consuming, even in expert hands, and carries a risk of traumatizing the uterus or adjacent organs. It is traumatic due to the nature of the suture, the diameter, the tension applied, and the suture-centric forces. The compressive strength is limited; it is applied only to the area of direct contact with suture. The risk of ischemia arises from the suture's failure to adjust after tightening.

Thus, an adjustable uterine compression apparatus for postpartum hemorrhage solving the aforementioned problems is desired.

SUMMARY

The adjustable uterine compression apparatus for postpartum hemorrhage includes at least one belt adapted for encircling the uterus transversely, the belt having keeper loops so that the belt can be cinched to continuously adjust the degree of compression applied to the uterus and the uterine arteries without losing the compressive effect. The belt may also be shortened and used to apply compression to the ovarian arteries. Preferably, a plurality of belts are applied spaced apart axially along the body and cervix of the uterus. The belts may be applied separately and independently, or may be embedded or incorporated into a sheet or vest that may be applied posteriorly behind the uterus and further secured by straps extending over the fundus that are cinched to at least one of the transverse belts to apply axial compression, in addition to transverse and anteroposterior compression of the uterus. The belt(s) and vest may be made of polyglactin mesh, so that they are bioabsorbable.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The adjustable uterine compression apparatus for postpartum hemorrhage includes at least one belt adapted for encircling the uterus transversely, the belt having keeper loops so that the belt can be cinched to continuously adjust the degree of compression applied to the uterus and the uterine arteries without losing the compressive effect. The belt may also be shortened and used to apply compression to the ovarian arteries. Preferably, a plurality of belts are applied spaced apart axially along the body and cervix of the uterus. The belts may be applied separately and independently, or may be embedded or incorporated into a sheet or vest that may be applied posteriorly behind the uterus and further secured by straps extending over the fundus that are cinched to at least one of the transverse belts to apply axial compression, in addition to transverse and anteroposterior compression of the uterus. The belt(s) and vest may be made of polyglactin mesh, so that they are bioabsorbable.

Figure 1:
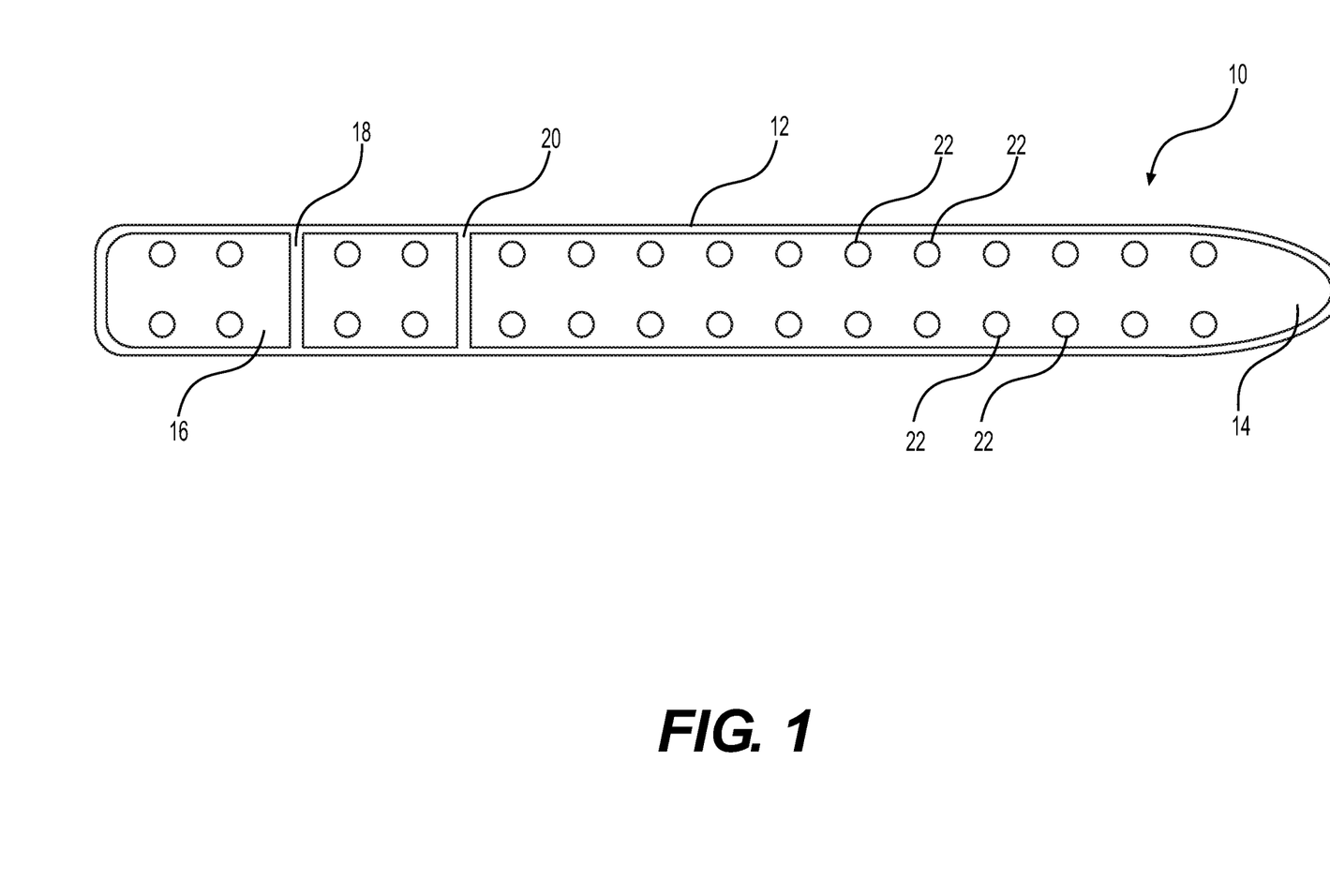
FIG. 1 is a front view of a first embodiment of an adjustable uterine compression apparatus for postpartum hemorrhage.
Figure 2:
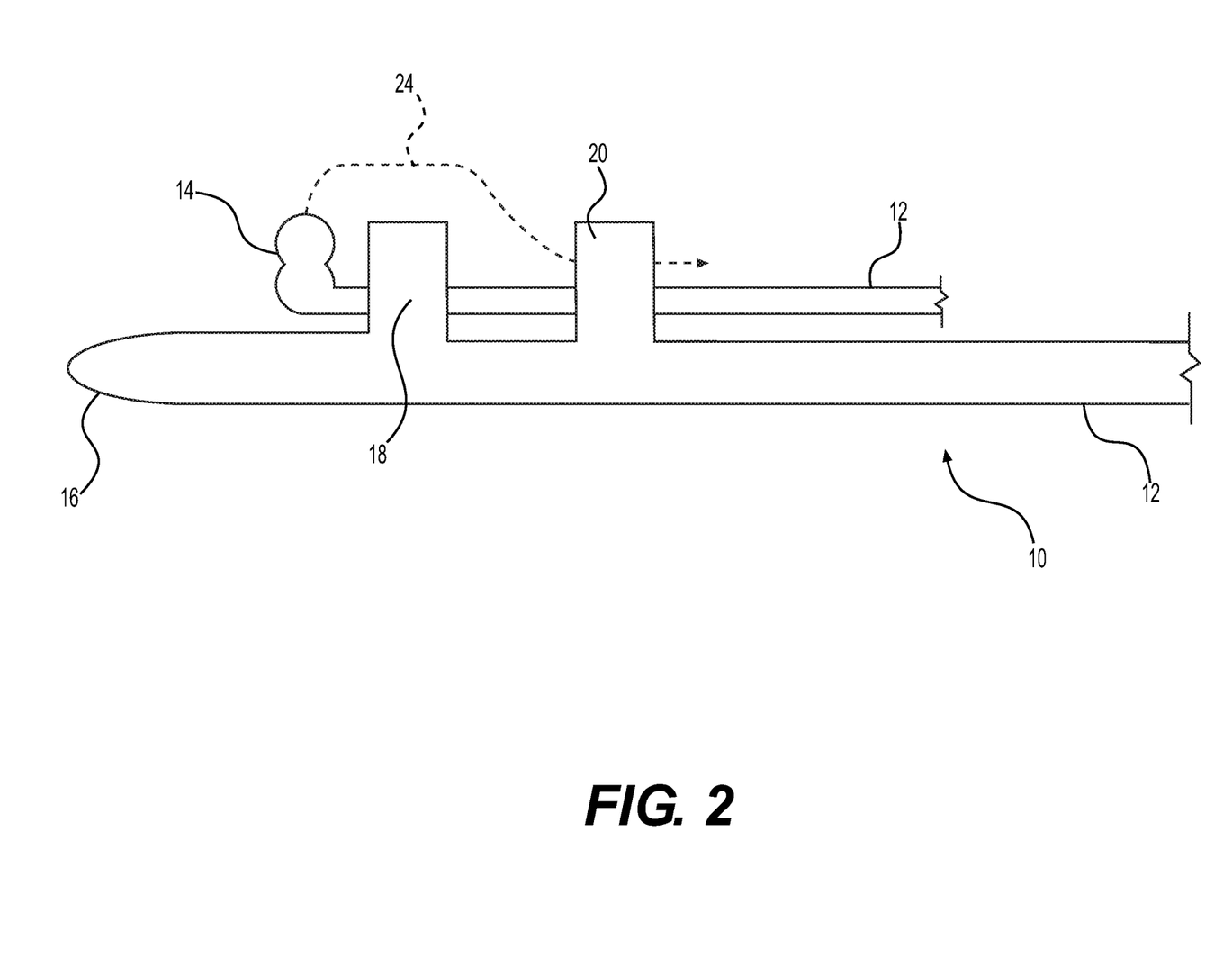
FIG. 2 is a partial side view of the adjustable uterine compression apparatus of FIG. 1, showing how the belt is cinched.
Figure 3:
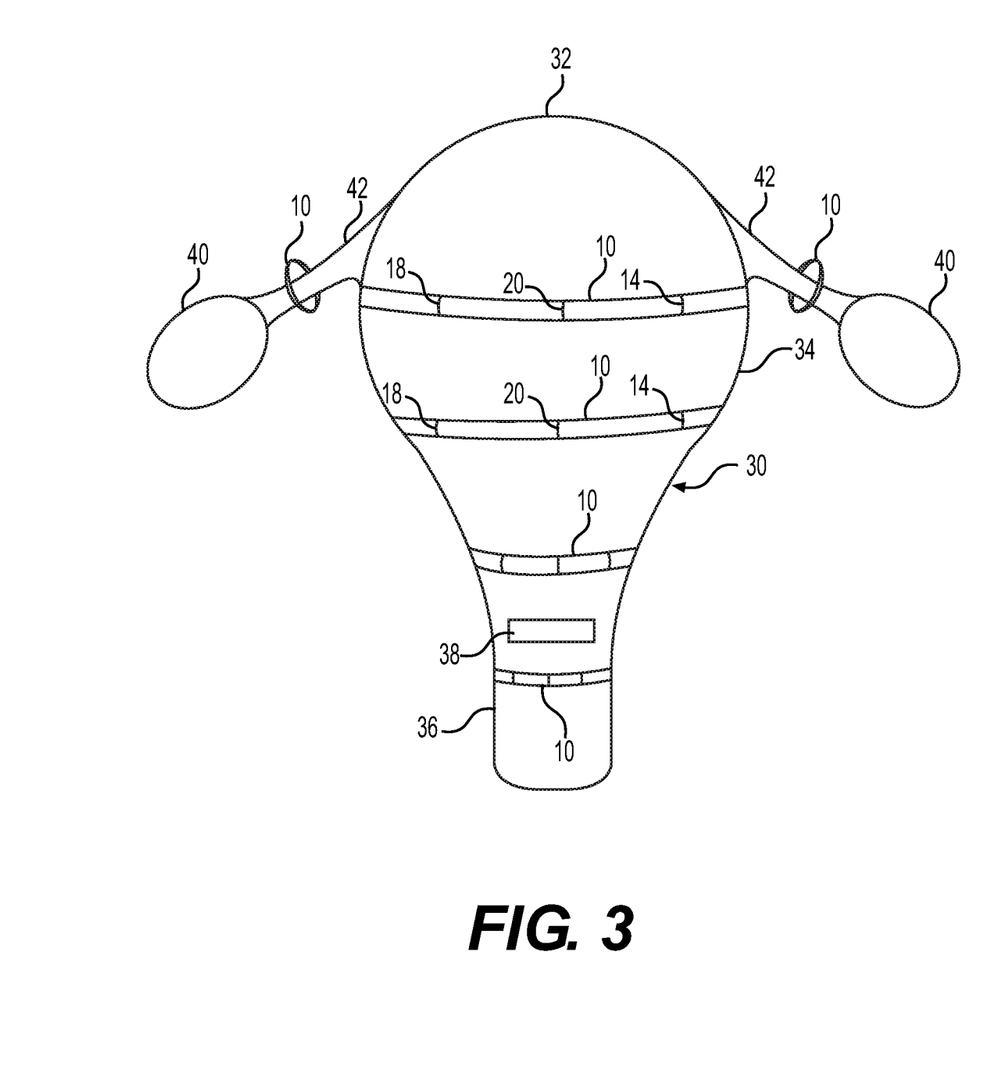
FIG. 3 is an environmental perspective view of multiple adjustable uterine compression apparatus of FIG. 1 cinched around the uterus at different levels and around the ovarian arteries.

As shown in FIGS. 1-3, in a first embodiment, the adjustable uterine compression apparatus 10 is an elongate belt 12 made of polyglactin mesh tape (or other bioabsorbable material) having a free end 14 and a cinching end 16. A pair of keeper loops, including a distal loop 18 and a medial loop 20, extend across one of the two opposing faces of the belt 12. A plurality of spaced apart pre-formed apertures 22 may be defined in the belt 12 extending beside opposing edges of the belt 12 to accommodate sutures to stabilize the belt, if needed. By way of example, the belt 12 may be one centimeter wide and thirty centimeters long, although actual dimensions may vary.

As shown in FIGS. 2 and 3, the belt 12 is adapted for wrapping around the uterus 30 one or more times (if required) at different levels and is secured to the uterus 30 by extending the free end through the two keeper loops 18 and 20, then wrapping the free end 14 over the distal loop 18 and under the medial loop 20. Compression is continuously adjusted by how tightly the free end is pulled through the distal loop 18 and under the medial loop 20 to cinch the belt 12.

As shown in FIG. 3, the uterus has a convex upper portion referred to as the fundus 32, a corpus or body 34 extending below the fundus 32, and a cervix 36 extending below the body 34. The ovarian arteries 42 may extend between the ovaries 40 and the fundus 32. Preferably, a first apparatus 10 is positioned around the uterus 30 between the fundus 32 and the corpus 34, a second apparatus 10 may be positioned around the corpus 34 between the fundus 32 and the cervix 36, and a third apparatus 10 may be positioned around the isthmus between the corpus 34 and the cervix 36. When the three apparatus 10 are cinched, compressive force is applied anteroposterior and laterally to the uterus, thereby compressing and squeezing the uterus and the uterine arteries extending down the sides of the uterus 30 to reduce the flow of blood from the uterus. When a C-section has been performed, so that there is an incision 38 in the area of the cervix 36, belts 10 may be placed approximately 2 cm above and below the incision to further reduce the flow of blood. In addition, the belt 12 may be shortened and cinched around the ovarian arteries 40 to restrict the flow of blood to the uterus 30.

Thus, in this embodiment, in the avascular segment of each of the broad ligaments, a small opening is made. Via these openings, the belt 12 is curved and fastened anterior to the uterus 30. For uterine atony, several belts 12 may be applied along the entire course of the uterine artery, and around the ovarian artery. During Caesarean section and for bleeding secondary to an abnormal placental location (Previa/Accreta), it is applied at the level of the uterine artery two cm below and above the lower segment uterine incision. Besides, multiple belts 12 can be applied, if needed, to cover the entire lower uterine segment, aiming to compress and squeeze the wall of the uterus and localized bleeding points at the area of its application, eliminating the need for blind hemostatic sutures. The apparatus 10 maximizes and enhances the function of intrauterine tamponades, such as the Bakri balloon. When paired, they provide a dual compression impact on the uterus. It improves balloon fitting and prevents it from slipping. We name this application the Uterine Corset Technique. The compression exerted from the belt 12 can be adjusted and sustained to prevent ischemia without losing the compression impact. The belts 12 can be administered prophylactically for any patient who bleeds more than 750 ml during Caesarean section.

The apparatus 10 enhances the efficiency and safety of postpartum hemorrhage management, compared with other surgical modalities, by its dual compression abilities, anteroposterior and lateral compression, the flexibility of application, and potential integration with other measures. It can address bleeding resulting from multiple pathologies, such as abnormal placentation conjugated with uterine atony. It reduces the bleeding by constricting the uterine wall and its blood supply bilaterally, with the potential to be re-adjusted as needed to prevent unnecessary pressure and avoid permanent ischemia, in addition to squeezing and direct compression impact on the wall of the uterus at the application area. It is flexible and can be applied at several levels, and around all the arteries supplying the uterus if needed. It is non-traumatic, less time consuming, simple to use, requires little expertise, and it may be blended with other procedures, such as intrauterine tamponades or extra surgical compression sutures. Nevertheless, the apparatus 10 may be loosened and left in place until the bleeding has been handled to prevent ischemia, but without losing the compression effect. The apparatus 10 provides flexible ability to concurrently compress the uterus and blood flow in postpartum hemorrhage cases that do not respond to conservative medical therapy.

Figure 4:
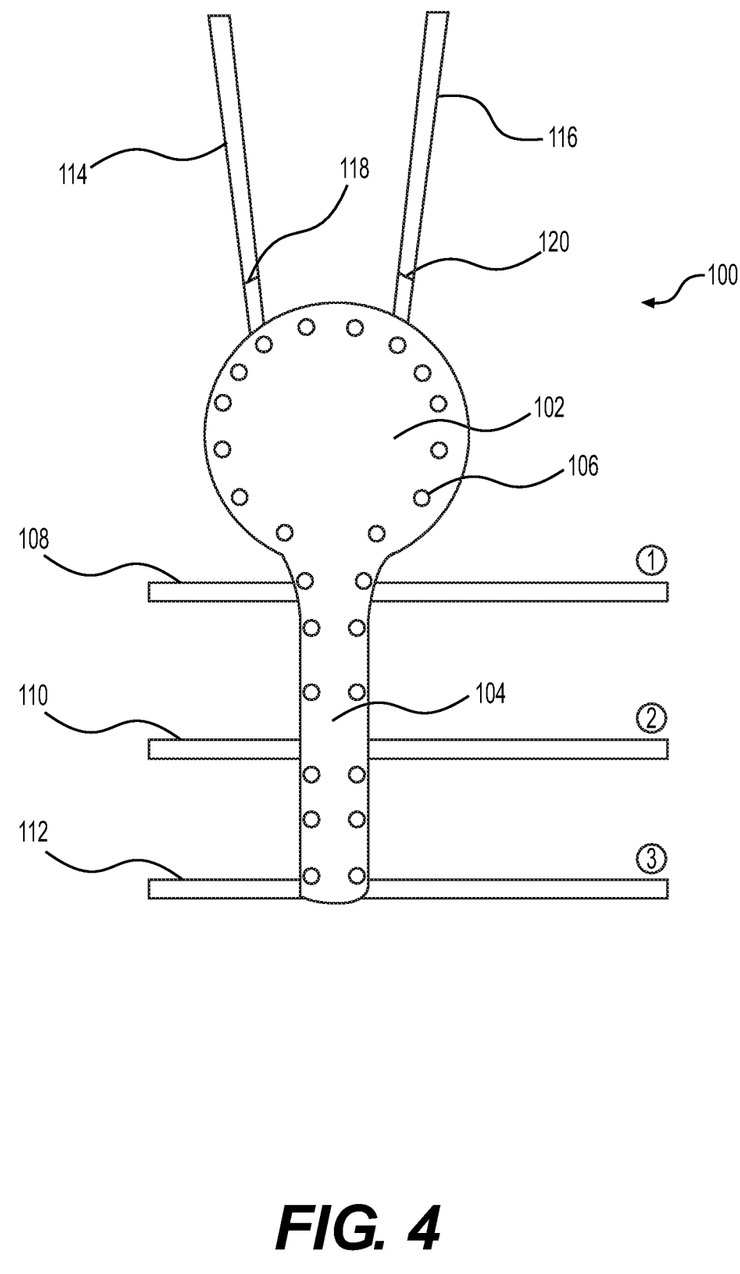
FIG. 4 is a rear view of a second embodiment of an adjustable uterine compression apparatus for postpartum hemorrhage.
Figure 5:
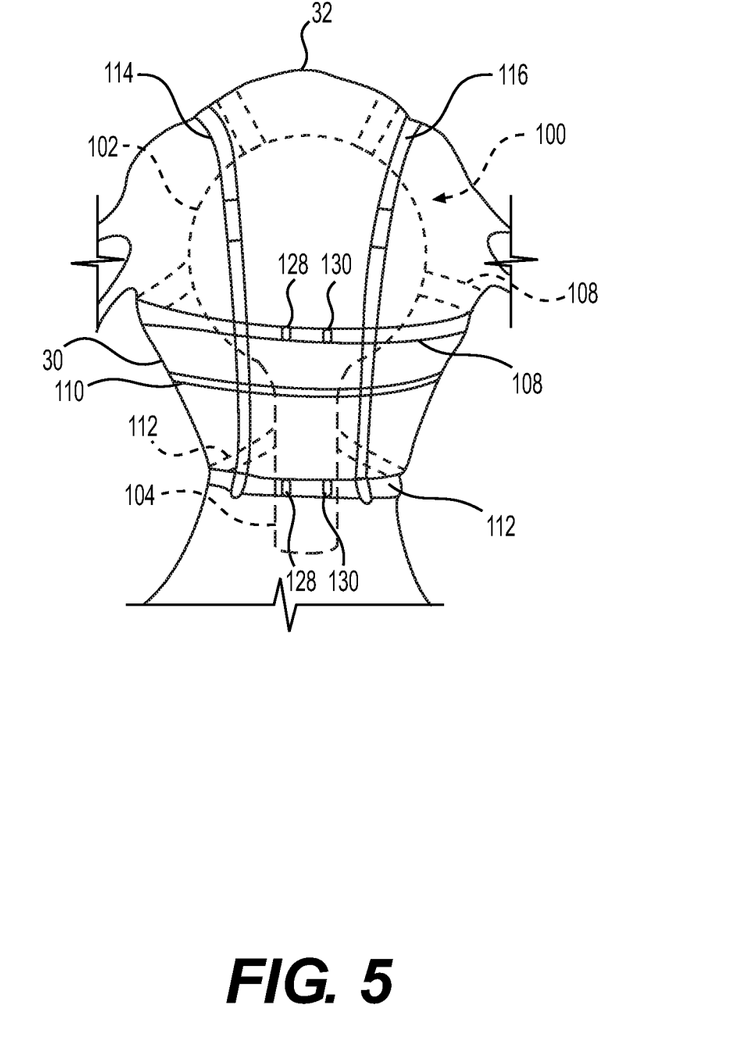
FIG. 5 is an environmental front view of the adjustable uterine compression apparatus of FIG. 4, shown cinched around the uterus.

FIGS. 4 and 5 show a second embodiment of an adjustable uterine compression apparatus 100. As shown in FIG. 4, the adjustable uterine compression apparatus 100 has a plurality of belts embedded or incorporated into a vest made of polyglactin mesh (or other bioabsorbable material. The embodiment of FIG. 4 has a broad body 102 to underlay the fundus 32 and corpus 34 of the uterus 30 and a narrower tail portion 104 to underlay the cervix 36, the body 102 and the tail 104 forming the vest, which has a top belt 108, a middle belt 110, and a lower belt 112 having a central portion partially embedded in or incorporated into the polyglactin mesh forming the body 102 and tail 104 of the vest, and a free end and a cinching end extending from opposite sides of the body 102 and/or tail 104. The body 102 and tail 104 may have a plurality of spaced apart pre-formed apertures 106 defined therein to accommodate sutures for stabilize the apparatus 100, if needed. The body 102 has a first strap 114 and a second strap 116 extending upward from the body. The strap 114 has at least one keeper loop 118 extending across a face of the strap 114, and the strap 116 also has at least one keeper loop 120 extending across the face of the strap 116. The straps 114 and 116 may have the same construction as the belts 12 of the first embodiment, being tapes made of polyglactin mesh.

As shown in FIG. 5, in use, the body 102 and tail 104 of the apparatus 100 are positioned behind or dorsal to the uterus 30. In the avascular segment of the broad ligament, below the ovarian ligament and two cm above and below the level of the uterine artery or lower transverse cesarean section incision, a small opening made. Through these openings, the belts 108, 110, and 112 are curved and fastened anterior to the uterus 30, the free ends of the belts 108, 110, and 112 being wrapped transversely around the uterus 30, the free ends being drawn through keeper loops 128 and 130, wrapped around the distal keeper loop 128 and cinched under the medial keeper loop 130 in the manner shown in FIG. 2. The straps 114 and 116 cross the fundus 32 of the uterus 30, compress it, pass under fastened belts 108, 110, and 112, and are cinched under the keeper loops 118 and 120. Thus, the apparatus 100 not only compresses the uterus laterally, but simultaneously applies compression to the uterus and its main blood supply axially and anteroposteriorly.

The apparatus 100 may be applied for postpartum hemorrhage where attempts at conservative medical treatment were unsuccessful before proceeding with other surgical interventions. It applies triple simultaneous axial, anteroposterior and lateral compression to the uterus and its main blood supply. For uterine atony, the apparatus 100 crowns, squeezes and compresses the uterus and its primary blood supply to avoid relaxation and blood filling. For bleeding secondary to an abnormal placental location, in addition to the compression effect on the uterus and uterine arteries, the application of the apparatus 100 ensures direct anteroposterior and lateral compression pressure on the lower uterine segment to reduce bleeding from placental beds without fear of harming the bladder or underlying tissues, and avoiding the need of blind hemostatic sutures. However, after bleeding has been managed, the compression exerted from the apparatus 100 can be adjusted and it may be kept in place to avoid ischemia, but without sacrificing the impact of compression. It can be paired with intrauterine tamponades, such as the Bakri balloon. The conjugation with intrauterine tamponade improves the efficacy of the tamponade by preventing it from falling, and at the same time, compresses the uterus and its blood supply; we name this approach the "Uterine Corset Technique".

Unlike other postpartum hemorrhage prevention approaches, the apparatus 100 is distinguished by its ability to cope simultaneously with various causes of bleeding at the same time, such as bleeding from abnormal placentation site conjugated with uterine atony. In comparison to hemostatic sutures and intrauterine tamponade, the apparatus 100 enhances the efficiency and safety of postpartum hemorrhage management through its multiple compression abilities, application flexibility, and the ability to integrate with other measures. It reduces the bleeding by compressing the uterus and constricting the whole course of uterine arteries simultaneously, with the potential to be re-adjusted, if needed, to prevent unnecessary pressure and avoid permanent ischemia without compromising the compression effect, in addition to squeezing and direct compression impact on the wall of the uterus at the application area. It is non-traumatic, causing little tension on the uterus. It is less time consuming, easy to use, doesn't require excessive skill, and integrates with other techniques, such as intrauterine tamponade or surgical compression sutures. However, after bleeding has been managed, the apparatus 100 can be loosened and kept in place to avoid ischemia, but without sacrificing the impact of compression.

Given its adjustable ability to simultaneously compress the uterus and its blood supply, apparatus 100 provides superior and additional value in cases of postpartum hemorrhage that do not respond to conservative medical treatment as a first-line procedure before proceeding with other measures. It can be administered prophylactically for any patient who bleeds more than 750 ml during Caesarean section.

It is to be understood that the adjustable uterine compression apparatus for postpartum hemorrhage is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An adjustable uterine compression apparatus for postpartum hemorrhage, comprising:
    a vest made of a bioabsorbable mesh sheet having a body portion adapted to underlay the fundus and corpus of a uterus and a tail portion being narrower in width than the body portion and extending lengthwise from the body portion and adapted to underlay the cervix, the body portion and tail portion of the vest being dimensioned and configured for positioning posterior to the uterus;
    a plurality of belts transversely spaced along the length of the tail portion, each of the belts having:
        a central portion embedded in the tail portion; and
        a free end and a cinching end extending laterally from opposite sides of the tail portion respectively, a plurality of keeper loops extending across one of the faces of the belt at the cinching end of the belt, the free end and the cinching end of each of the belts being wrapped transversely around the uterus and cinched together via the plurality of keeper loops to secure the apparatus to the uterus and apply compression to reduce or stop bleeding from postpartum hemorrhage; and a plurality of elongated straps extending upwardly from the body portion of the vest, each of the straps having at least one keeper loop attached across the strap, the straps being dimensioned and configured for wrapping over the fundus of the uterus and under the ends of each of the belts, and returned to cinch under the strap keeper loops, whereby the apparatus applies compression to the uterus laterally, axially, and antero-posteriorly.

2. The adjustable uterine compression apparatus according to claim 1, wherein said belts and said straps are made of the bioabsorbable material.

3. The adjustable uterine compression apparatus according to claim 2, wherein said bioabsorbable material comprises polyglactin.

4. The adjustable uterine compression apparatus according to claim 1, wherein each of the body portion and tail portion have a plurality of spaced apart pre-formed apertures defined therein extending along their entire length adjacent edges thereof.

* * * * *